United States Patent [19]

Imwinkelried et al.

[11] Patent Number: 4,812,476

[45] Date of Patent: Mar. 14, 1989

[54] PROCESS FOR STEREOSECTIVELY PREPARING OPTICALLY ACTIVE COMPOUNDS

[75] Inventors: René Imwinkelried, Fiesch; Dieter Seebach, Zurich, both of Switzerland

[73] Assignee: Imperial Chemical Industries PLC, London, England

[21] Appl. No.: 906,736

[22] Filed: Sep. 9, 1986

[30] Foreign Application Priority Data

Oct. 17, 1985 [GB] United Kingdom ............... 8525666

[51] Int. Cl.$^4$ ............................................. C07C 59/48
[52] U.S. Cl. ............................. 562/470; 562/579; 562/580; 562/588; 558/451
[58] Field of Search ............... 562/470, 580, 579, 588

[56] References Cited

PUBLICATIONS

Chem. Abs. 102:35189v.
Chem. Abs. 90:95408j.
"Conformational Analysis-V 2.6 Dialkyl- and 2.2.6-Trialkyl-4-Oxo-1.3-Dioxans", *Tetrahedron*, vol. 29, pp. 1311-1316 (1973).
"4-Oxo-1,3-Dioxan and its Methyl Derivatives", *Tetrahedron Letters*, No. 47, pp. 4095-4096 (1970).

*Primary Examiner*—Paul J. Killos
*Attorney, Agent, or Firm*—Cushman, Darby & Cushman

[57] ABSTRACT

An aldehyde ($R^1$CHO) and optically active 3-hydroxybutyric acid ($CH_3CH(OH)CH_2COOH$) are reacted to form an optically active dioxanone. This dioxanone is reacted with a compound $R^2$—X to form an intermediate ($R^1R^2$CHOCH($CH_3$) $CH_2$COOH) which is then subjected to elimination to form an optically active secondary alcohol ($R^1R^2$CHOH) in good yield and purity.

8 Claims, No Drawings

PROCESS FOR STEREOSECTIVELY PREPARING OPTICALLY ACTIVE COMPOUNDS

The present invention relates to a process for preparing secondary alcohols and to intermediates useful in such a process. In particular this invention relates to preparing secondary alcohols in enantiomerically pure or highly enriched form.

Secondary alcohols are sought after compounds, either having beneficial end uses or being important intermediates in organic synthesis. A large number of methods are known to those skilled in the art for preparing secondary alcohols and many of these methods lead to enantiomerically pure or enriched material; for example the asymmetric reduction of ketones; the asymmetric addition of nucleophiles to aldehydes; the asymmetric epoxidation of allylic alcohols with subsequent ring opening; kinetic resolution such as with esterases; and asymmetric substitution on acetal centres. These methods have various disadvantages such as the necessity of multistep conversions to the secondary alcohol after the asymmetric reaction; expensive asymmetric reagents; and maximum theoretical yield of 50%.

One particularly attractive method of the art is the asymmetric substitution of an alkoxy group on an acetal centre:

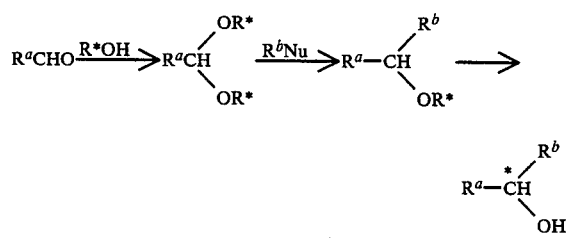

Features of this method are that it can provide high selectivity, high yields and can be of general applicability. However there are numerous disadvantages associated with this method. The chiral alcohol R*OH can be expensive to use, particularly on a commercial scale, and is destroyed in the overall process. In addition various authors (Richter, J. Org. Chem., 46, 5119 (1981); McNamara et al., J.A.C.S., 104, 7371 (1982); Bartlett et al., J.A.C.S. 105, 2088 (1983); Ghribi et al., Tet. Lett. 3083 (1984); Elliott et al., Tet. Lett., 2535 (1985); Mori et al., J. Organomet. Chem., 285, 83 (1985); Fujiwara et al. J.A.C.S., 106, 5004 (1984); and Mashraqui et al., J. Org. Chem. 49, 2313 (1984)) have found poor yields in the preparation of the acetal, unsatisfactory selectivity, the reaction is extremely sensitive to changes in conditions, the conversion of the group R*O— to hydroxy is difficult and separation of by-products may require chromatography, and the leaving groups in the asymmetric substitution are constitutionally identical.

We have provided an improved solution, to these problems of the art, that makes use of cheap readily available chiral starting materials, gives good stereoselectivity and generally easy purification, and is particularly convenient for large scale synthesis.

Accordingly the present invention provides a process for stereoselectively preparing an optically active compound of the formula (I):

wherein $R^1$ and $R^2$ are independently organic groups, and differ from each other, which comprises the steps of:

(i) reacting a compound of the formula (II) and an optically active compound of the formula (III) or a derivative thereof:

$$R^1CHO \quad (II)$$

$$CH_3CH(OH)CH_2COOH \quad (III)$$

wherein $R^1$ is as hereinbefore defined, to form an optically active compound of the formula (IV):

wherein $R^1$ is as hereinbefore defined, (ii) reacting a compound of the formula (IV) with a compound of the formula (V):

$$R^2-X \quad (V)$$

wherein $R^2$ is as hereinbefore defined and X is a leaving group, to form an optically active compound of the formula (VI) or derivative thereof:

$$R^1R^2CH-O-CH(CH_3)CH_2COOH \quad (VI)$$

wherein $R^1$ and $R^2$ are as hereinbefore defined, and (iii) eliminating $R^1R^2CH-OH$ from the compound of the formula (VI).

Suitably $R^1$ is $C_{1-10}$ hydrocarbyl, for example $C_{1-10}$ alkyl, $C_{2-10}$ alkenyl, $C_{2-10}$ alkynyl, aryl, aryl ($C_{1-4}$) alkyl, $C_{3-10}$ cycloalkyl, $C_{3-7}$ cycloalkyl ($C_{1-4}$) alkyl, heteroaryl, heteroaryl ($C_{1-4}$) alkyl, aryl ($C_{2-4}$) alkenyl, aryl ($C_{2-4}$) alkynyl, heteroaryl ($C_{2-4}$) alkynyl, heteroaryl ($C_{2-4}$) alkenyl, heterocyclyl, heterocyclyl ($C_{1-4}$) alkyl, heterocyclyl ($C_{2-4}$) alkenyl or heterocyclyl ($C_{2-4}$) alkynyl; any of such groups being optionally substituted. Suitably the hetero atoms in the heterocyclyl and heteroaryl moieties are selected from 1 to 4 oxygen, sulphur or nitrogen atoms, the ring systems preferably containing 5 or 6 ring atoms.

Suitable substituents for the group $R^1$ include $C_{1-10}$ alkyl, $C_{2-10}$ alkenyl, $C_{1-10}$ alkylamino, di($C_{1-10}$) alkylamino, amino, hydroxy, $C_{1-10}$ alkoxy, mercapto, $C_{1-10}$ alkylthio, halo, nitro, carboxy and the like.

Particular values of $R^1$ are $C_{1-10}$ alkyl and phenyl($C_{1-4}$)alkyl. Preferably $R^1$ is methyl, ethyl, isopropyl, tert-butyl, trichloromethyl, benzylphenyl or phenethyl.

The compound of the formula (III) is readily available in either R- or S-configuration and is a convenient inexpensive starting-material for the process of this invention.

(R)-3-Hydroxybutanoic acid is readily available by the depolymerisation of the microbiologically synthesised poly(R)-3-hydroxybutanoic acid (PHB). For details of such depolymerisation see Seebach et Züger, Helv. Chim. Acta. 65 495 (1982).

(S)-3-Hydroxybutanoic acid is readily available by yeast reduction of acetoacetic ester, see Seebach et al., Organic Syntheses 63, 1 (1984).

The readily available chiral 3-hydroxybutanoic acids have been disclosed as useful, cheap starting materials in a number of synthetic methods, see for example Seidel et Seebach, Tet. Lett. 2209 (1984) and the references contained therein.

The compound of the formula (III) is conveniently obtained and used as an acid; if it is preferred to use it in the form of a salt or ester then such derivatives can be obtained in a conventional manner. Conveniently the compound of the formula (III) is used in the form of a silyl derivative for example the bis trimethylsilyl derivative.

The reaction between the compounds of the formulae (II) and (III) suitably may be performed at ambient or elevated temperature in a solvent. Suitable solvents include halogenated and aromatic hydrocarbons. Preferably for secondary and tertiary aldehydes of the formula (II) an aromatic hydrocarbon such as benzene or toluene is used. Preferably for primary aldehydes of the formula (II) chloroform or dichloromethane is used. Conveniently the reaction is performed at reflux with the water formed during the reaction being collected via a Dean-Stark apparatus or the like. The reaction is performed in the presence of a catalyst, for example an acidic catalyst such as sulphuric acid or toluene-4-sulphonic acid.

The dioxanone products of the formula IV are generally produced in a diastereomeric mixture having a ratio of about 9:1. This mixture can be readily purified in conventional manner, but often can be used in the next step of the process of this invention without any ensuing substantial loss of optical purity of the final product.

The reaction of compounds of the formulae (IV) and (V) is performed in the presence of a Lewis acid catalyst. Suitable catalysts include boron, aluminium and titanium derived catalysts, for example boron trifluoride, aluminium chloride, titanium tetrachloride and ($C_{1-4}$) alkoxytitanium chlorides such as isopropoxytitanium trichloride, di-isopropoxytitanium dichloride and tri-isopropoxytitanium chloride. Of these the titanium derived catalysts are preferred. Although they all give beneficial results we have found that the ($C_{1-4}$) alkoxytitanium trichlorides, in particular isopropoxytitanium trichloride, are considerably more selective.

Suitably $R^2$ is $C_{1-6}$ alkyl, $C_{2-6}$ alkenyl, $C_{2-6}$ alkynyl, or any of such groups substituted by aryl, heteroaryl or heterocyclyl as defined hereinbefore. Suitably also $R^2$ can be cyano. X is a leaving group, suitably a silyl moiety such as trimethylsilyl or a cuprate moiety.

The reaction of the compounds of the formulae (IV) and (V) is generally performed at a depressed temperature, in a substantially inert solvent, such as a halogenated hydrocarbon.

It is found that the substitution by the $R^2$-group is determined by the superior leaving group ability of the ester-type as compared to the ether-type oxygen of the dioxanone. Therefore optically active β-hydroxyacids of the formula (VI) are formed.

The optically active compounds of the formula (VI) and their derivatives are novel and therefore form part of the present invention.

Therefore in another aspect of the present invention there is provided a process for preparing a compound of the formula (VI) or a derivative thereof as hereinbefore defined which comprises reacting compounds of the formulae (IV) and (V) as hereinbefore defined.

The present invention also provides the use of the compounds of the formula (VI) or a derivative thereof. Therefor in a further aspect of the present invention there is provided a process for preparing a compound of the formula (I) as hereinbefore defined which comprises treating a compound of the formula (VI) or derivative thereof with base to effect elimination.

The elimination of the product secondary alcohol $R^1R^2$CHOH from the compound of the formula (VI) can be performed in conventional manner using basic elimination forming a crotonic acid as a by-product. Such elimination is suitably carried out in a substantially inert solvent, suitably an ether such as tetrahydrofuran or dioxan, at a depressed temperature for example between 0° C. and −78° C. The base is suitably a strong non-nucleophilic base such as lithium di-isopropylamide.

The following Examples serve to illustrate the invention.

EXAMPLE 1

(R)-6-Phenyl-1-hexen-4-ol (a) A mixture of (R)-3-hydroxybutanoic acid (7.8 g), 3-phenylpropionaldehyde (6.71 g) and pyridinium toluene-4-sulphonic acid (ca. 10 mmol %) in dichloromethane (300 ml) was stirred, under reflux, for 48 hours with removal of water. The reaction mixture was cooled to room temperature, washed three times with saturated sodium bicarbonate, dried (MgSO$_4$) and evaporated under reduced pressure. The residue was crystallised from ether/pentane to give (2R,6R)-2-(2'-phenylethyl)-6-methyl-1,3-dioxan-4-one (7.0 g), m.p. 49.7°–50.9° C.; $[\alpha]_D^{R.T.} = 15.2 (c=1.05; CHCl_3)$.

(b) Part of the product from (a) above (2.2 g) and trimethyl allylsilane (3 equivalents) were cooled to −78° C. in dichloromethane (20 ml). To this cooled solution was added titanium tetrachloride (1.2 equivalents) (1M in dichloromethane). The resultant mixture was warmed to room temperature and hydrolysed with dilute hydrochloric acid. The crude product was extracted into diethyl ether, dried (MgSO$_4$) and evaporated under reduced pressure to give as an oil, (3R,5R)-5-(2'-phenylethyl)-3-methyl-4-oxa-oct-7-enoic acid (2.5 g); $[\alpha]_D^{R.T.} = 6.58 (c=2.29; CHCl_3)$: diastereomeric ratio 87%:

IR: 3520(w); 3080(w); 3010(m); 2990(m); 2940(s); 1755(m); 1715(s); 1640(w); 1600(w); 1490(w); 1380(m); 1340(m); 1310(m); 1135(m); 1080(m); 1035(m); 700(m).

$^1$H-NMR: 1.2 (d, J=6, 3H, CH$_3$); 1.58-1.96 (m, 2H, CH$_2$—CHO); 2.13-2.84 (m, 6H, CH$_2$—COO, Ph—CH$_2$, CH$_2$—C=C; 3.42 (qu, J=6, 1H, O—CH); 3.92 (sex. J=6, 1H, CH—Me); 4.88-5.18 (M, 2H, CH$_2$=C); 5.51-6.05 (m, 1H, —CH=C); 7.18 (s, 5H, arom.); 9.98-10.89 (br, 1H, COOH).

This reaction was also performed in good yield using TiCl$_3$(OPr$^i$), TiCl$_2$(OPr$^i$)$_2$ and TiCl(OPr$^i$)$_3$.

(c) Part of the product from (b) above (0.722 g) was cooled to −30° C. in tetrahydrofuran (6 ml). To this stirred solution was added lithium di-isopropylamide (2.2 equivalents) (ca 0.8M in tetrahydrofuran/hexane (1:1)). The resultant mixture was warmed to room temperature over 3 hours, hydrolysed with dilute hydrochloric acid and extracted into ether. The ether extracts were washed with saturated sodium bicarbonate, dried (MgSO$_4$) and evaporated under reduced pressure to give as an oil, after flash chromatography, (R)-6-phenyl-1-hexen-4-ol (0.362 g); $[\alpha]_D^{R.T.}=15.7°$ (c=1.39; CHCl$_3$); enantiomeric excess=74%:

$^1$H-NMR: 1.60-1.91 (m, 2H, CH$_2$); 2.1-2.52 (m, 3H, CH$_2$—Ph and OH); 2.56-2.92 (m, 2H, CH$_2$—C=); 3.42-3.78 (m, 1H, CH—O); 4.92-5.22 (m, 2H, CH$_2$=C); 5.55-6.03 (m, 1H, CH=C); 7.16 (s, 5H, arom.).

EXAMPLES 2a–6a.

In a manner similar to Example 1a, the following dioxanones were obtained in good yield *3-HB is 3-HB is 3-hydroxybutanoic acid.

| Ex. | Chiral starting-Material | Aldehyde | Dioxanone |
|---|---|---|---|
| 2a | (R)—3-HB | CH$_3$(CH$_2$)$_6$CHO | (CH$_2$)$_6$CH$_3$ dioxanone |
| 3a | (R)—3-HB | (CH$_3$)$_3$CCHO | C(CH$_3$)$_3$ dioxanone |
| 4a | (R)—3-HB | (CH$_3$)$_2$CHCHO | CH(CH$_3$)$_2$ dioxanone |
| 5a | (R)—3-HB | Cl$_3$CCHO | CCl$_3$ dioxanone |
| 6a | (S)—3-HB | C$_6$H$_5$CH$_2$CH$_2$CHO | (CH$_2$)$_2$C$_6$H$_5$ dioxanone |

EXAMPLES 2b–6b

In a manner similar to Example 1b, the dioxanones (2a–6a) were reacted with trimethylallylsilane to give the respective β-alkoxyacids.

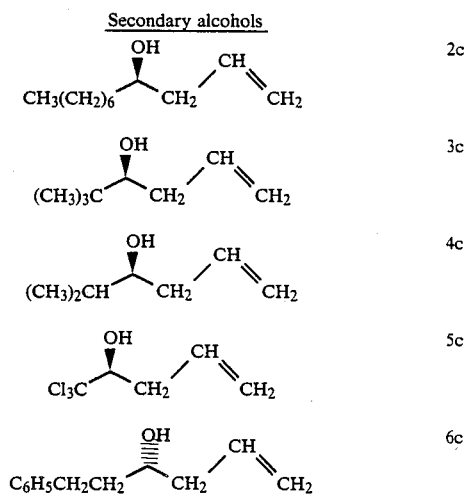

EXAMPLES 2c–6c

In a manner similar to Example 1c, the β-alkoxy acids (2b–6b) undergo a basic elimination to give the respective secondary alcohols.

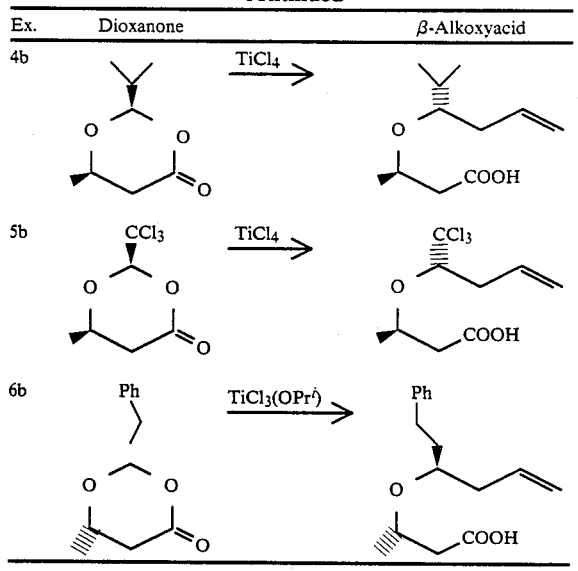

Characterising data for Compounds 2a–6c (2a) (2R,6R)-2-Heptyl-6-methyl-1,3-dioxan-4-one, Diastereomerically pure, m.pt ca −20° C., $[\alpha]_D^{R.T.}=-33.2$ (c=1.85; CHCl$_3$).

IR: (CHCl$_3$) 2970(m); 2940(s); 2870(m); 1740(s); 1460(w); 1390(m); 1350(s); 1290(m); 1260(s); 980(s).

$^1$H-NMR (300 MHz): 0.858-0.904 (m, 3H, CH$_3$—CH$_2$); 1.262-1.480 (m, 10H, 5 CH$_2$); 1.328 (d, J=6.148, 3H, CH$_3$—); 1.739-1.81 (m, 2H, CH$_2$—C—O); 2.372 (d×d, J$_1$=17.72, J$_2$-10.68, 1H, H—CH); 2.655 (d×d, J$_1$=10.69, J$_2$=4.34, 1H, HC—$\underline{\text{H}}$); 4.009 (d×d×q, J$_1$=10.68, J$_2$=4.34, J$_3$=6.148, 1H, Me—CH); 5.295 (t, J=5.014, 1H, O—CH—O).

(3a) (2R,6R)-2-(t-Butyl)-6-methyl-1,3dioxan-4-one, Diastereomerically pure, m.pt 82.2°-82.8° C., $[\alpha]_D^{R.T.}=-56.56°$ (c=1.28; CHCl$_3$).

(4a) (2R,6R)-2-Isopropyl-6-methyl-1,3-dioxan-4-one,

Diastereomeric ratio 96%; colourless oil; $[\alpha]_D^{R.T.}=55.7°$ (c=1.53; CHCl$_3$).

IR: 2980(m); 2940(w); 2910(w); 2880(w); 1740(s); 1470(w); 1380(m); 1340(m); 1285(m); 1250(s); 1220(m); 1165(m); 985(s); 960(m); 750(m).

$^1$H-NMR (300 MHz): 0.995 (d, J=6.88, 3H, CH$_3$); 1.004 (d, J=6.87, 3H, CH$_3$); 1.327 (d, J=6.12, 3H, CH$_3$); 1.925-2.031 (m, 1H, CHMe$_2$); 2.366 (d×d, J$_1$=17.70, J$_2$=10.67, 1H, H—CH); 2.657 (d×d, J$_1$=17.70, J$_2$=4.36, 1H, HC—H); 3.997 (d×d×q, J$_1$=10.67, J$_2$4.36, J$_3$=6.12, 1H, Me—CH—O); 5.076 (d, J=4.3, 1H, O—CH—O).

(5a) (2R,6R)-6-Methyl-2-trichloromethyl-1,3-dioxan-4-one

Diastereomerically pure white crystals, m.pt 113.6°-114.4° C.; $[\alpha]_D^{RT}=-54.7°$ (c=1.62; CHCl$_3$).

(6a) (2S,6S)-2-(2'-Phenylethyl)-6-methyl-1,3-dioxan-4-one

Diastereomerically pure white crystals, m.pt 49.5°-50.4° C.; $[\alpha]_D^{RT}=15.4°$ (c=0.47; CHCl$_3$).

(2b) (3R,5R)-5-Heptyl-3-methyl-4-oxa-oct-7-enoic acid

Diastereomeric ratio 82%; $[\alpha]_D^{RT}=-9.55°$ (c=1.57; CHCl$_3$).

IR: (CHCl$_3$) 3520(w); 2950(s); 2870(m); 1760(m); 1720(s); 1640(w); 1610(w); 1380(m); 1340(w); 1310(w); 1130(m); 1090(m); 1005(m); 920(m).

$^1$H-NMR: 0.8-1.04 (m, 3H, CH$_3$); 1.18-1.60 (m, 15H, CH$_3$—(CH$_2$)$_6$); 2.24 (t, J=6, 2H, CH$_2$COO); 2.36-2.64 (m, 2H, CH$_2$—C=); 3.27-3.58 (m, 1H, O—CH); 4.09 (sex, J=6, 1H, Me—CH); 4.91-5.18 (m, 2H, CH$_2$=C); 5.58-6.03 (m, 1H, —CH=C; 9.52-10.07 (br, 1H, COOH).

(3b) 3R,5S-5-(t-Butyl)-3-methyl-4-oxa-oct-7-enoic acid

Diastereomeric ratio: 62%. $[\alpha]_D^{RT}=12.3°$ (c=0.95; CHCl$_3$).

IR: (CHCl$_3$) 3540(w); 2990(s); 2880(m); 1760(s); 1720(s); 1640(w); 1430(w); 1400(m); 1370(m); 1340(w); 1305(w); 1135(m); 1090(s); 1075(s); 1020(m); 1005(m); 920(m).

$^1$H-NMR: 0.88 (s, 9H, C(CH$_3$)$_3$); 1.20 (d, J=6, 3H, CH$_3$); 2.10-2.84 (m, 4H, 2 CH$_2$); 2.98-3.18 (m, 1H, CH—O); 3.82-4.10 (m, 1H, Me—CH); 4.89-5.20 (m, 2H, CH$_2$=C); 5.64-6.13 (m, 1H, =CH—C); 10.68-10.96 (br, 1H, COOH).

(4b) (3R,5S)-5-Isopropyl-3-methyl-4-oxa-oct-7-enoic acid

Diastereomeric ratio: 75%. $[\alpha]_D^{RT}=-23.8°$ (c=1.01; CHCl$_3$).

IR: 3180(shoulder); 3080(m); 2970(s); 2930(m); 2880(m); 1710(s); 1640(m); 1430(m); 1375(m); 1300(s); 1210(s); 1075(s); 1035(s); 1020(m); 995(m); 910(s).

$^1$H-NMR: 0.86 (d, J=6, 6H, C(CH$_3$)$_2$); 1.18 (d, J=6, 3H, CH$_3$); 1.62-2.03 (m, 1H, Me—CH—Me); 2.08-2.82 (m, 4H, 2 CH$_2$); 3.28 (q, J=6, 1H, CH—O); 3.91 (sex, J=6, 1H, Me—CH); 4.86-5.16 (m, 2H, CH$_2$=C); 5.52-6.08 (m, 1H —CH=C); 10.7-11.22 (br, 1H, COOH).

(5b) (3R,5S)-3-Methyl-4-oxa-5-trichloromethyl-oct-7-enoic acid

Diastereomeric purity 92%. $[\alpha]_D^{RT}=-42.1°$ (c=1.09; CHCl$_3$).

IR: 3700-2400 (broad); 3080(m); 2980(s); 2930(m); 1710(s); 1640(m); 1430(m); 1410(m); 1380(m); 1335(m); 1300(m); 1210(m); 1100(s); 990(m); 920(m); 780(s).

$^1$H-NMR: 1.21 (d, J=6, 3H, CH$_3$); 2.24-2.98 (m, 4H, 2 CH$_2$); 3.94 (d×d, J$_1$=3, J$_2$=3, 1H, CH—CCl$_3$); 4.42 (sex, J=6, 1H, CH—Me); 5.02-5.3 (m, 2H, CH$_2$=C); 5.60-6.12 (m, 1H, —CH=); 10.92-11.36 (br, 1H, COOH).

(2c) (R)-1-Undecen-4-ol $[\alpha]_D^{RT}=5°$ (c=2.12; CHCl$_3$); enantiomeric excess=60%.

$^1$H-NMR: 0.77-1.02 (m, 3H, CH$_3$); 1.13-1.62 (m, 12H, —(CH$_2$)$_6$—); 2.10-2.43 (m, 3H, CH$_2$—C= and OH); 3.48-3.77 (m, 1H, CH—O); 4.92-5.21 (m, 2H, CH$_2$=C); 5.56-6.08 (m, 1H, —CH=).

(5c) (S)-5,5,5-Trichloro-1-penten-4-ol

Oil. $^1$H-NMR: 1.21 (d, J=6, 3H, CH$_3$); 2.18-3.02 (m, 4H, 2 CH$_2$); 3.66 (s, 3H, O—CH$_3$); 3.78-4.04 (m, 1H, CH—CCl$_3$); 4.44 (sex, J=6, 1H, Me—CH); 4.94-5.33 (m, 2H,CH$_2$=C; 5.55-6.12 (m, 1H, —CH=C).

(6c) (S)-6-Phenyl-1-hexen-4-ol

Colourless oil. $[\alpha]_D^{RT}=-20.4°$ (c=2.42, CHCl$_3$).

EXAMPLE 7

(2R,6R)-2-(2'-Phenylethyl)-6-methyl-1,3-dioxan-4-one (Example 1a) was reacted with:
(i) (CH$_3$)$_3$Si—CN
(ii) (CH$_3$)$_3$Si—C≡CH
(iii) (CH$_3$)$_3$Si—C≡C—CH$_3$
(iv) (CH$_3$)$_3$Si—CH$_2$COOC$_2$H$_5$
to give respectively:

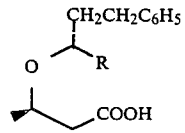

(i) R=CN
(ii) R=C≡CH
(iii) R=—C≡C—CH$_3$
(iv) R=—CH$_2$COOC$_2$H$_5$

These β-alkoxyacids were reacted with lithium diisopropylamide to give respectively:

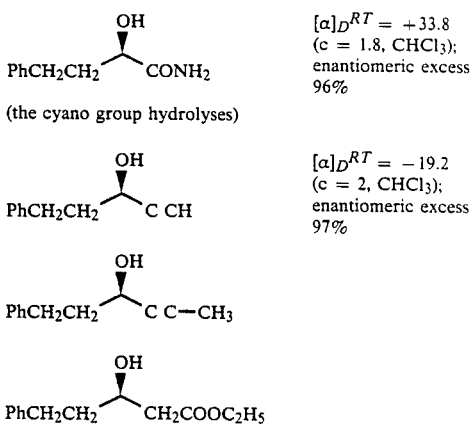

(i) PhCH$_2$CH$_2$—C(OH)—CONH$_2$    $[\alpha]_D^{RT}=+33.8$ (c = 1.8, CHCl$_3$); enantiomeric excess 96%
(the cyano group hydrolyses)

(ii) PhCH$_2$CH$_2$—C(OH)—C CH    $[\alpha]_D^{RT}=-19.2$ (c = 2, CHCl$_3$); enantiomeric excess 97%

(iii) PhCH$_2$CH$_2$—C(OH)—C C—CH$_3$ (iv) PhCH$_2$CH$_2$—C(OH)—CH$_2$COOC$_2$H$_5$

EXAMPLE 8

(2R,6R)-2,6-Dimethyl-1,2-dioxan-4-one was reacted with trimethylsilylcyanide, the resultant nitrile hydrolysed to form the amide and then subjected to b-elimination to give (R)-2-hydoxypropionamide

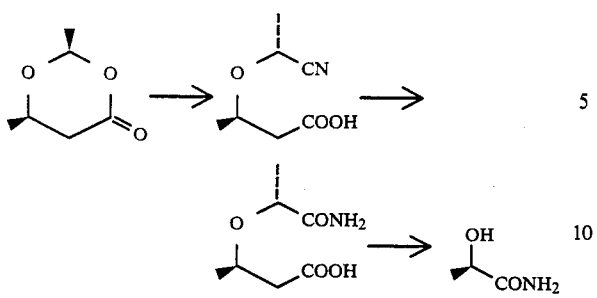

EXAMPLE 9

To a suspension of (R)-3-hydroxybutyric acid (174 mmol) in dichloromethane (200 ml) was added triethylamine (385 mmol) at 0°–5° C. under an argon atmosphere. Trimethylsilyl chloride (385 mmol) was added dropwise to the solution at 0°–5° C. The resultant suspension was stirred at room temperature for 2 days, then diluted with pentane (150 ml), filtered and the filtrate evaporated under reduced pressure to yield a residue. This residue was taken up in pentane (100 ml), filtered and again evaporated under reduced pressure. The resultant residue, a yellow liquid, was purified through a short-path distillation (60°/0.15 mm) to yield (R)-O,O'-bis(trimethylsilyl)-3-hydroxybutyric acid (40.5 g; 94%) as a colourless liquid. This is stored under argon at low temperature.

EXAMPLE 10

To a cold solution (−75° C.) of (R)-O,O'-bis(trimethylsilyl)-3-hydroxybutyric acid (1.1 equivalents) and an aldehyde (1.0 equivalent) is added trimethylsilyl triflate (0.02 equivalents). The solution is stirred at −75° C. for 10–20 hours and then pyridine (0.1 equivalents) is added. The mixture is warmed to room temperature, extracted once with saturated sodium bicarbonate, dried (MgSO₄) and filtered. The solvent is removed by evaporation under reduced pressure to give the 1,3-dioxan-4-one in good yields and very good purity. The product is generally a mixture of cis/trans isomers typically in a ratio of about 97:3.

Typical aldehyde used are:
PhCH₂CH₂CHO: 81% yield
(CH₃)₃CHO: 65% yield
PhCHO: 84% yield

What is claimed is:
1. A process for stereoselectively preparing an optically active compound of the formula (I):

wherein R₁ is an organic group selected from the class consisting of substituted C$_{1-10}$ hydrocarbyl groups and unsubstituted C$_{1-10}$ hydrocarbyl groups and wherein R₂ is an organic group selected from the class consisting of C$_{1-6}$ alkyl, C$_{2-6}$ alkenyl, C$_{2-6}$ alkynyl which can be substituted by any aryl, heteroaryl and heterocyclyl groups and cyano groups and R¹ and R² differ from each other, (i) reacting a compound of the formula (II) and an optically active compound of the formula (III) or a derivative thereof at ambient or elevated temperatures, in a solvent, and in the presence of a suitable catalyst:

wherein R¹ is as above defined, to form an optically active compound of the formula (IV):

wherein R¹ is as above defined,
(ii) reacting a compound of the formula (IV) with a compound of the formula (V) in the presence of a Lewis acid catalyst:

wherein R² is as above defined and X is a leaving group, to form an optically active compound of the formula (VI) or derivative thereof:

wherein R¹ and R² are as above defined, and
(iii) eliminating optically active compound R¹R²CHOH from the compound of the formula (VI) by reaction of the compound fo the formula (VI) with a base, in a substantially inert solvent at a depressed temperature.

2. A process according to claim 1 wherein R¹ is C$_{1-10}$ alkyl, aryl or aryl(C$_{1-4}$)alkyl.

3. A process according to claim 1 wherein R¹ is methyl, ethyl, isopropyl, tert-butyl, trichloromethyl, benzyl, phenyl or phenethyl.

4. A process according to claim 1 wherein R² is C$_{1-6}$ alkyl, C$_{2-6}$ alkenyl, C$_{2-6}$ alkynyl or cyano.

5. A process according to claim 4 wherein R² is allyl.

6. A process according to claim 1 wherein the compound of the formula (III) is reacted in the form of a bis silyl derivative.

7. A process according to claim 1 wherein X is a silyl moiety.

8. A process according to claim 1 wherein the compounds of the formulae (IV) and (V) are reacted in the presence of a titanium derived catalyst.

* * * * *